United States Patent
Torres

[11] Patent Number: 5,544,812
[45] Date of Patent: Aug. 13, 1996

[54] TABLE-TOP AIR FRESHENER

[76] Inventor: David F. Torres, Ctra. Nacional 340 Km. 118, 04230 Huercal De Almeria (Almeria-Spain), Spain

[21] Appl. No.: 102,827

[22] Filed: Aug. 6, 1993

[30] Foreign Application Priority Data

Aug. 7, 1992 [ES] Spain .................................. 9202490

[51] Int. Cl.$^6$ ..................................................... A61L 9/12
[52] U.S. Cl. ................... 239/55; 239/57; 239/58; 239/211; 428/905; D23/367; D23/369
[58] Field of Search ................... 239/34, 53–55, 239/57, 58, 60, 211; 428/905, 18, 19; D23/367, 369; 403/349, 245, 251, 360

[56] References Cited

U.S. PATENT DOCUMENTS

| | | | |
|---|---|---|---|
| 1,294,304 | 2/1919 | Pittman | 403/349 |
| 1,469,104 | 9/1923 | Ornduff | 239/57 |
| 2,283,028 | 5/1942 | Bailey | 239/57 |
| 2,734,769 | 2/1956 | Holz | 239/57 |
| 2,763,395 | 9/1956 | Meek | 239/58 |
| 3,065,915 | 11/1962 | Samann | 239/58 |
| 3,908,906 | 9/1975 | Crowle et al. | 239/58 |
| 3,910,495 | 10/1975 | Cummings et al. | 239/58 |
| 4,279,373 | 7/1981 | Montealegre | 239/57 |
| 4,898,328 | 2/1990 | Fox et al. | 239/34 |

FOREIGN PATENT DOCUMENTS

| | | | |
|---|---|---|---|
| 3223780 | 3/1983 | Germany | 239/58 |

Primary Examiner—Karen B. Merritt
Attorney, Agent, or Firm—Jacobson, Price, Holman & Stern, PLLC

[57] ABSTRACT

A table-top air freshener has a tubular cylinder containing perfume-impregnated cellulose strips. The cylinder press-fits into a cylindrical cavity formed in a decorative housing with the bottom of the cylinder exposed for attachment to a stand. A selected length of the cylinder can be withdrawn from the cavity to provide a desired perfuming effect.

4 Claims, 3 Drawing Sheets

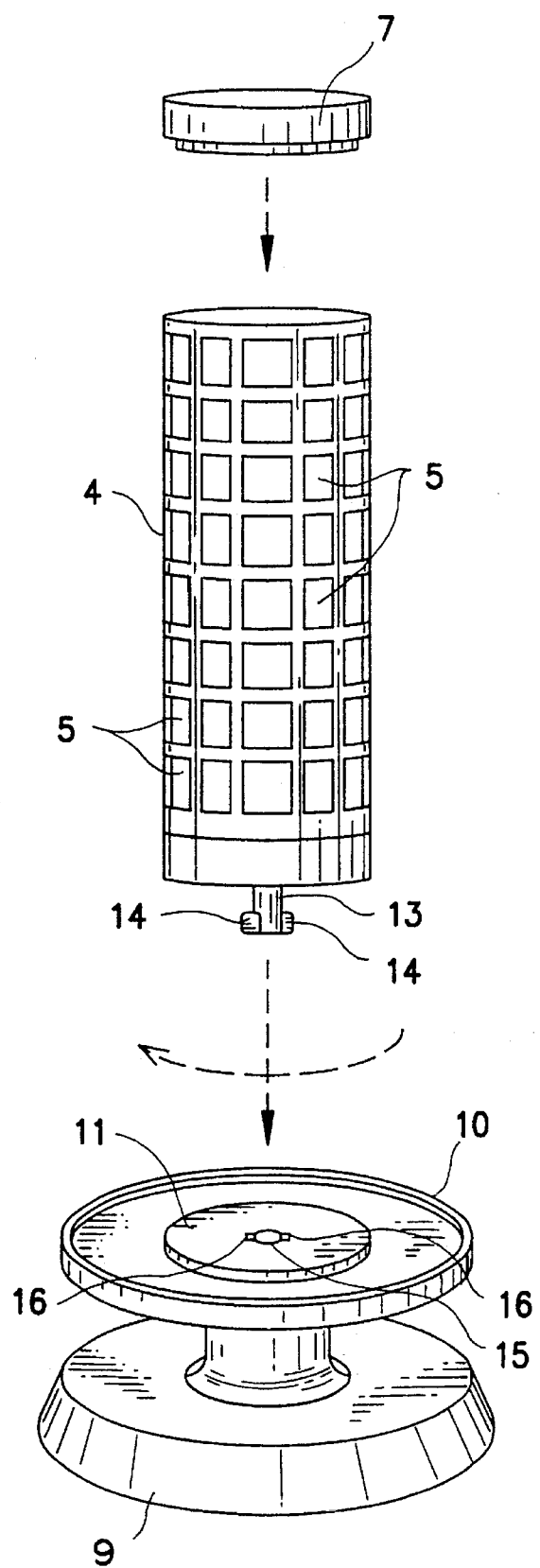
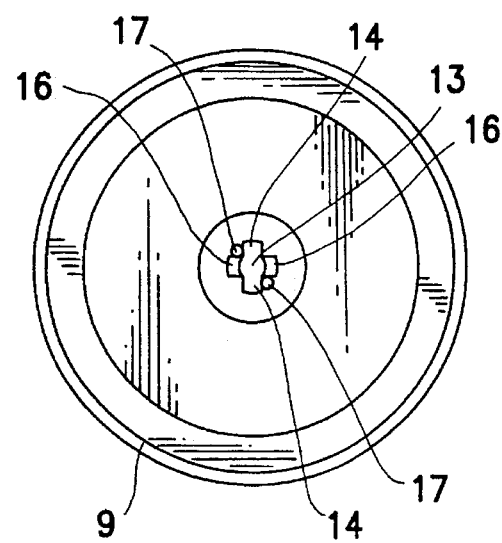
FIG. 6
FIG. 7

TABLE-TOP AIR FRESHENER

SUMMARY OF THE INVENTION

This invention relates to a new table-top air freshener which provides unquestionable benefits and improvements of a practical and decorative nature, being made up of three parts which fit together, namely an outer, decorative part with the external form of a pine or fir tree, a removable interior element which is the freshener itself, in the form of a tubular cylinder whose whole surface comprises a number of evaporation openings through which the perfume in said hollow cylinder can emerge, and a third element comprising the stand of the perfumer, in the form of a plinth into whose top the non-stop perfume dispenser cylinder is fitted.

The perfuming element consists of a number of cellulose strip rods which are impregnated with the perfume, and which are placed inside the cylinder, which is then closed with a pressure-fitted cover or plug.

One of the important benefits of this system is the use of cellulose strips or rods, which increases the perfume support surface, unlike existing models already on the market, which use whole cellulose strips. With the increase in the perfume support surface, thanks to the cellulose rods, the dispersal of the perfume itself is enhanced: this is a vital characteristic of air fresheners.

The cylinder with the cellulose rods, duly perfumed and placed inside and plugged closed, forms a separate unit which is easily replaced once the perfuming function is finished.

At the bottom of said cylinder which is housed with its freshener rods in the base, there is a rib on the entire perimeter around the cylinder, which is pressure-fitted into a groove on the perimeter of the top shelf on the freshener base.

The cylinder can alternatively be fitted to the base with a lug emerging from the centre of its underside, which is pressure-fitted and turned into place in an opening through the base itself, by means of protruding radial lugs.

Another most important benefit of this system is the ease with which cylinders are replaced when the perfume in the originals is finished without, despite such simplicity, bringing the user into contact with the perfume.

The system's perfume intensity is controlled by raising or lowering the other part on the assembly comprising the base and perfume cylinder. The two assemblies—other part and base/cylinder—are sufficiently tight to enable them, for this control, to be placed in any position of greater or lesser height and graduation: the two elements are hermetically sealed by a dovetail system for the coupling of the two assemblies.

Apart from that benefit of this model's system, emphasis must be placed on the novelty of this freshener as a decorative element, with a design whose features evoke Nature at the same time as perfuming: the other part may be green, while the base is in a wood-tone of brown.

The tabletop air freshener which is the subject of the invention has structural and constituent elements which are completely different from the various fresheners currently known.

BRIEF DESCRIPTION OF THE DRAWINGS

FIG. 6 is a perspective view of the different elements projected on a vertical axis, showing the assembly formed by the top cover of the pressure-fitted cylinder which carries the group of cellulose rods impregnated with the perfuming component, and with the perfume evaporation openings; this design is varied in the attachment to the base, with a central lug emerging from the underside of the central cylinder, and protruding radial wings on two diametrically opposed points which fit into a central opening in the base, locking merely by turning.

FIG. 7 is lower face view of the support base, showing the lock system as in FIG. 6, with the internal lugs which act as lock stops.

DESCRIPTION OF THE PREFERRED EMBODIMENT

Figure 1:
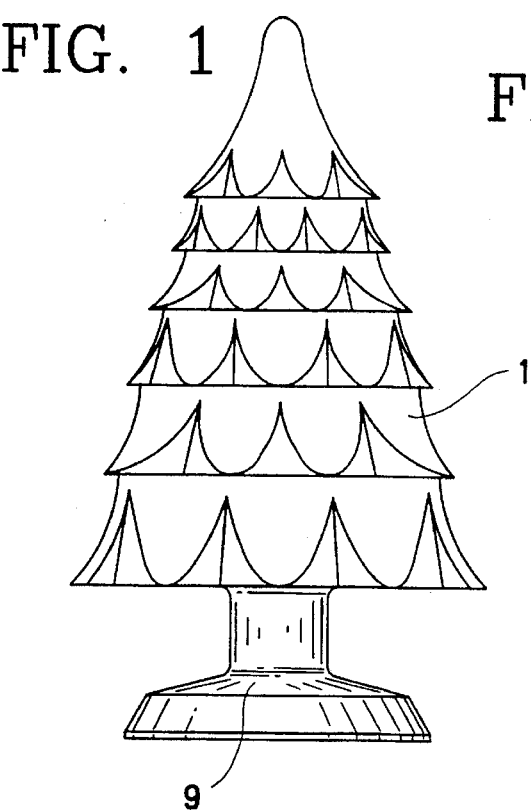
FIG. 1 is a front elevation view of the table-top air freshener, assembled and completely closed, so that it will not operate as such air freshener.
Figure 2:
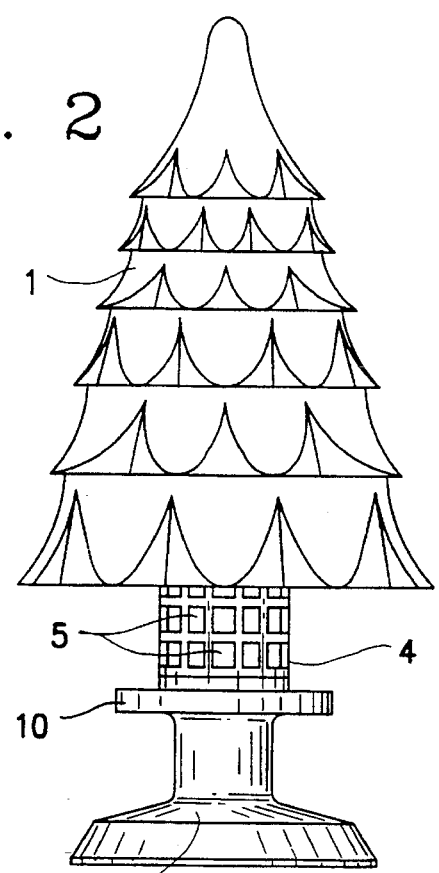
FIG. 2 is front elevation view as in FIG. 1, but with the base partly extracted so that, through the openings in the hollow cylinder, the perfume can be dispersed outward from the cellulose rods.
Figure 4:
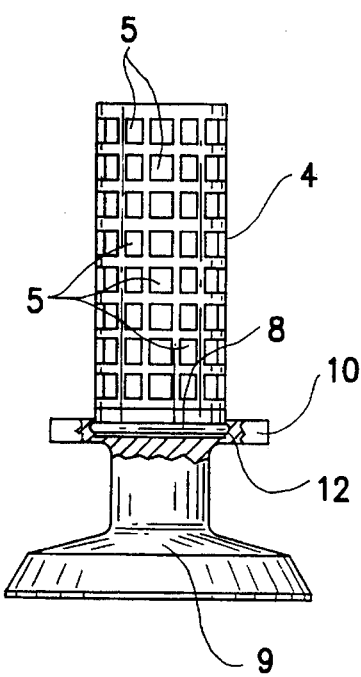
FIG. 4 is elevation view of the inside element comprising a hollow cylinder with a number of evaporation openings over its peripheral surface from which the perfume emerges from cellulose rods where it is stored: said piece is pressure-fitted into the bottom of the freshener by means of a peripheral protruding ring in the base or plinth of the air freshener.
Figure 3:
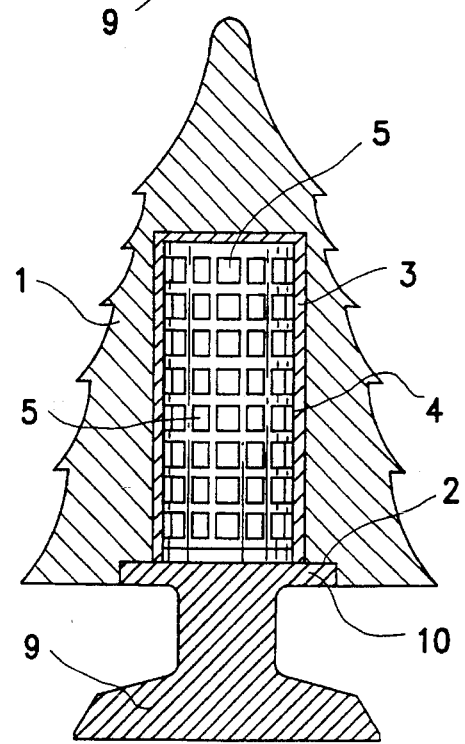
FIG. 3 is general diametrical elevated cross-section of FIG. 1, showing the housing for the hollow cylinder with the perfumer and the hermetic dovetail seal of the disc forming part of the base, inside a housing in the bottom of the pine unit.
Figure 5:
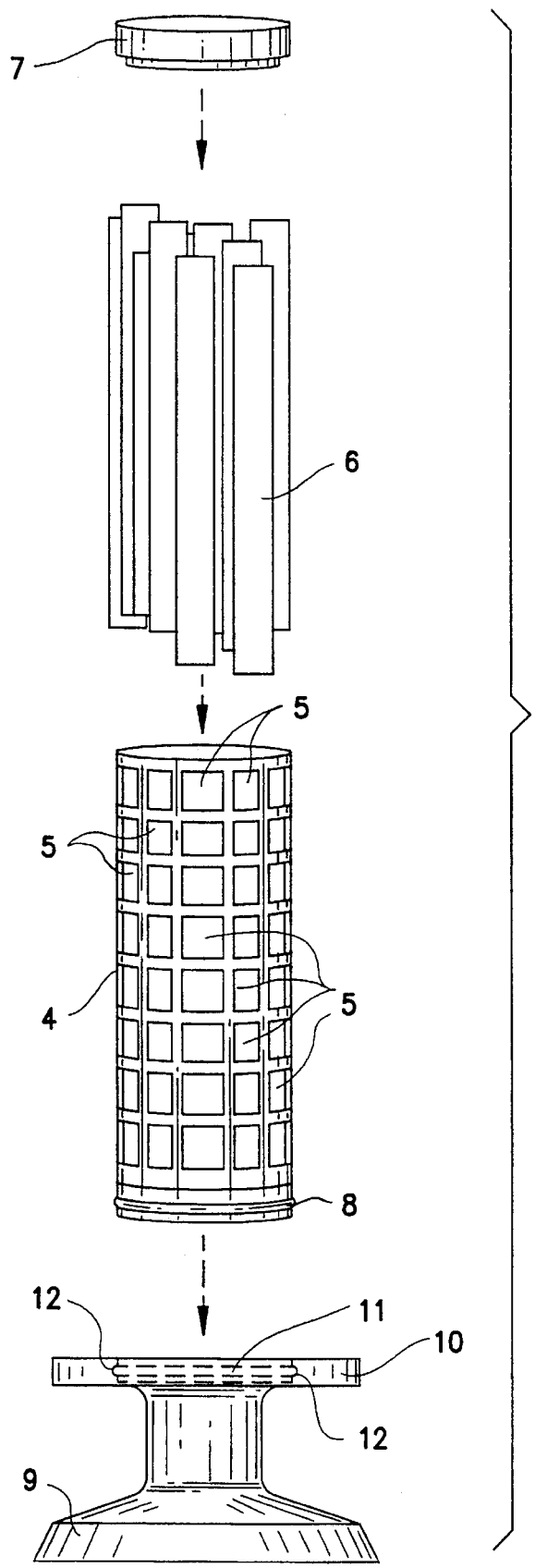
FIG. 5 is a perspective view of the different elements projected on a vertical axis of the assembly forming the upper cover of the cylinder, which is pressure-fitted, the group of cellulose rods impregnated with the perfuming component and housed inside the central cylinder, the central cylinder itself with the perfume evaporation openings and the base ring around said cylinder in the form of a rib, the base of the table-top air freshener pine with the central female housing and the peripheral groove which receives the protruding ring on the cylinder.

With reference to said attached drawings, it must be recorded that the figures there incorporate numerical references related to the descriptions given below of their characteristics and operation, thereby facilitating their immediate location. The external housing -1- may take the form of a pine, fir or any other tree, preferably green, in the base of which there is, in the first instance, a circular cavity -2- followed by another of smaller diameter and greater depth in which to adjust the internal bush -3- for the tight movement of the perfuming cylinder tube -4- inside it.

The air freshener unit is formed by said cylindrical tube -4- which has a number of evaporation openings -5- over the whole of its periphery from which to disperse the perfume impregnated into the cellulose rod -6-, inside said cylinder -4-: the area is closed by the top cover -7- which is tightly pressure fitted. There is a slightly protruding ring around the bottom of the freshener cylinder -4-, forming a changeable air freshener assembly.

The support base -9- of the air freshener, preferably of brown wood colour, consists of the upper disc -10- coupled into the circular cavity -2- of the external housing -1- of the housing 1. In the centre of its upper face it has a circular cavity -11- in which to fit the bottom end of the cylinder -4-, with an internal peripheral groove -12- in which to pressure fit the protruding ring -8- which forms part of said tubular cylinder -4-, for easy removal and replacement when the perfuming product has lost its effect.

The perfuming effect of this air freshener is controlled by raising or lowering the housing -1- on the assembly of the base -9- and cylinder -4-: these two moveable units are sufficiently pressure-fitted so that, as the height is adjusted, they will always remain in the position required by the user.

As a variation of the procedure to lock the cylinder -4- in the base -9- to the cylinder -4- in the centre of its bottom surface, it has the protruding axial lug -13- with radial wings -14- arranged on diametrically opposite points and which fit into the central opening -15- with the grooves -16-, so that the wings -14- emerge inside the base -9-, turning it until said wings stop against the inside lugs -17- in the table-top base of the air freshener.

With this comprehensive description of each and every one of the parts making up the table-top air freshener which is the subject of the invention, it remains only to be said that the different elements may be made in a variety of materials, sizes, shapes and colours, and that the construction may be altered as practice would suggest, provided that this does not modify the essential points to which this registration is referred.

I claim:

1. An air freshener comprising a tubular cylinder having a closed bottom, a peripheral wall and a top, plural openings in said wall for outward transmission of perfume from the cylinder, a perfume element within said cylinder comprising a plurality of cellulose strips impregnated with perfume, and a cover for the top of the cylinder; said air freshener including a housing for the cylinder, said housing having a cylindrical cavity to receive the cylinder with a press-fit and with the bottom of the cylinder exposed at one end of the cavity whereby the cylinder can be withdrawn from the cavity to a selected length to provide a required perfuming effect, a stand for supporting the cylinder and housing on a support surface, and releasable attachment means on the stand and on the bottom of the cylinder.

2. An air freshener as claimed in claim 1, wherein the housing is formed to simulate a tree.

3. An air freshener as claimed in claim 1, wherein the attachment means comprises a peripheral annular rib around the bottom of the cylinder, an aperture in the stand to receive the bottom of the cylinder and an annular recess around a peripheral wall of said aperture to receive said rib.

4. An air freshener as claimed in claim 1, wherein the attachment means comprises a projecting hub with peripheral lugs on the bottom of the cylinder and a correspondingly shaped aperture in the stand to receive said hubs and provide attachment of the cylinder and stand by rotation of the hub in said aperture.

* * * * *